United States Patent [19]

Weissman

[11] Patent Number: 4,538,987
[45] Date of Patent: Sep. 3, 1985

[54] DENTAL DIE TRAY ASSEMBLY

[75] Inventor: Bernard Weissman, New York, N.Y.

[73] Assignee: Ipco Corporation, White Plains, N.Y.

[21] Appl. No.: 534,812

[22] Filed: Sep. 22, 1983

[51] Int. Cl.³ .............................................. A61C 19/00
[52] U.S. Cl. ........................................ 433/60; 433/34; 249/54
[58] Field of Search ...................... 249/54; 433/34, 60, 433/45; 425/79

[56] References Cited

U.S. PATENT DOCUMENTS

| | | | |
|---|---|---|---|
| 1,377,075 | 5/1921 | Homer | 433/34 |
| 3,221,408 | 12/1965 | Scullin | 433/60 |
| 4,022,419 | 5/1977 | Haker | 249/54 |
| 4,283,173 | 8/1981 | Browne | 433/34 |

Primary Examiner—Hugh R. Chamblee
Assistant Examiner—K. McNamara
Attorney, Agent, or Firm—Goodman & Teitelbaum

[57] ABSTRACT

A dental die tray assembly for the production of a dental working model for use in producing a prosthetic dental device, the assembly including a die tray body member having upper and lower surfaces, and a peripheral outer wall. A hollow arcuate mold cavity extends entirely through the body member in an outwardly widening direction from the lower surface to the upper surface. The mold cavity is bounded by facing outer and inner walls, with the outer cavity wall being foreshortened by a recessed seat bounding an outer periphery of the mold cavity. Continuous teeth are disposed on the facing cavity walls and extend into the mold cavity. A pair of removable arms are pivotally coupled to respective side portions of the peripheral outer wall of the die tray body member and embrace at least a portion of the body member circumscribing the mold cavity to releasably hold the model in the mold cavity. A reversible base plate member includes a substantially flat base surface on one side thereof which serves as a bottom for the mold cavity during the formation of the model, and further includes pusher members protruding from the opposite side thereof for ejecting the model from the mold cavity after the model has been completed.

33 Claims, 16 Drawing Figures

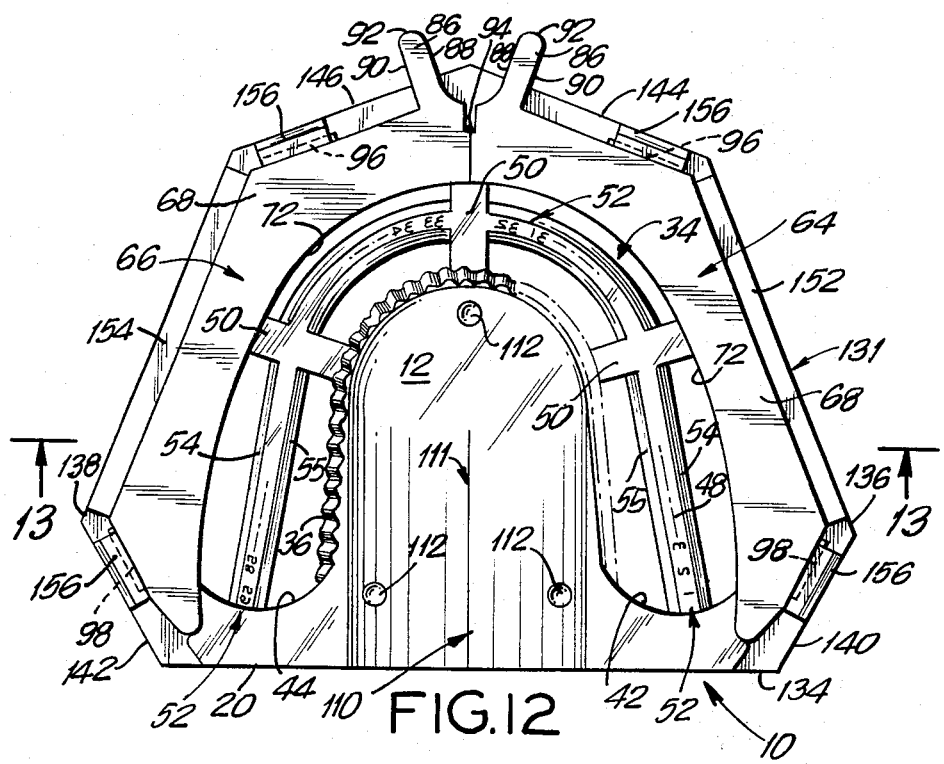
FIG.12
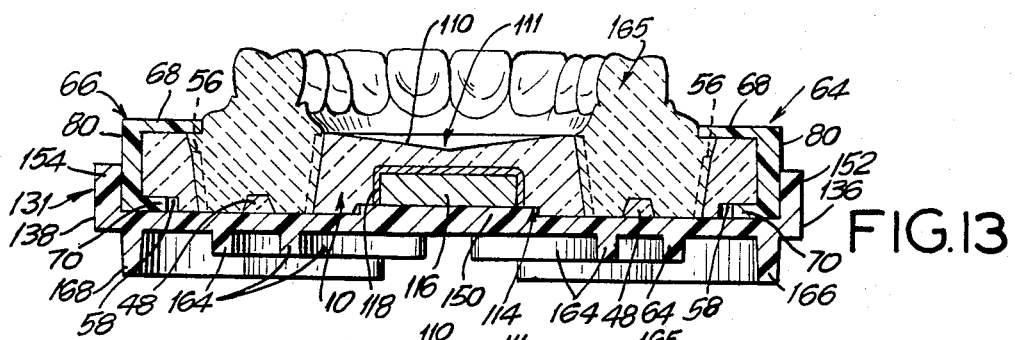
FIG.13
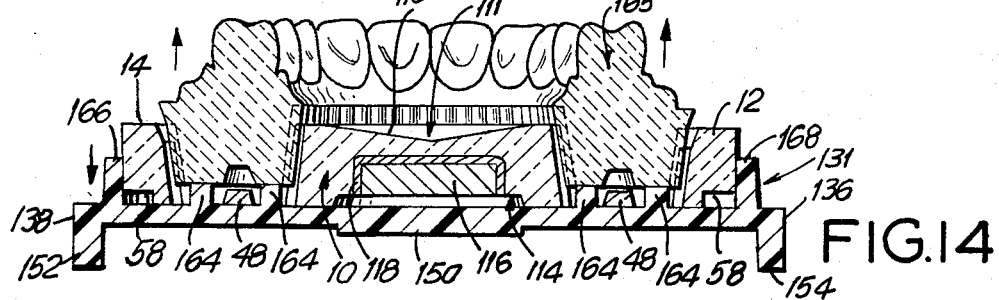
FIG.14
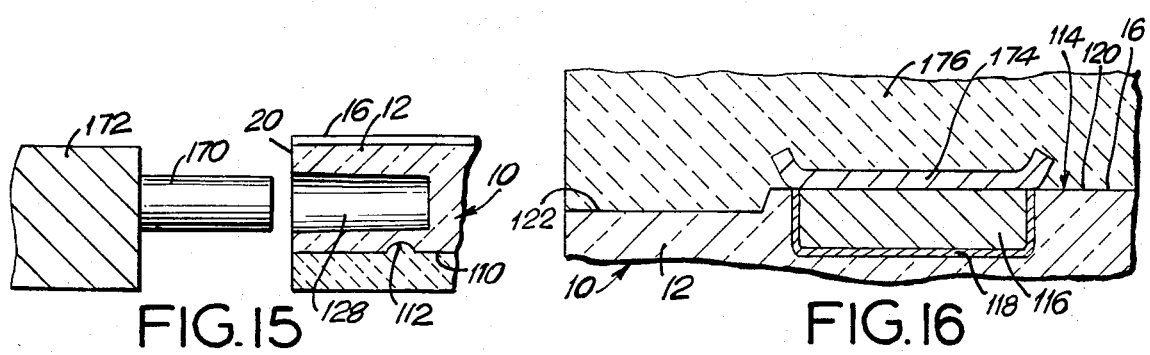
FIG.15
FIG.16

DENTAL DIE TRAY ASSEMBLY

BACKGROUND OF THE INVENTION

This invention relates to dental trays for the production of a dental working model used for the preparation of a dental prosthesis.

In connection with the production of tooth crowns, tooth bridges, and the like, it is general procedure to form a casting mold which is used as a model base in the formation of the dental prosthesis. Dental die trays are frequently utilized for this purpose. The tray includes a mold cavity for use in the preparation of the model. Typically, after an imprint has been produced by the dentist in which the prepared teeth as well as possibly the gum, mandible portions, palate, etc. are imprinted, the imprint which represents the negative is filled by a special plaster mass at the laboratory or at the dental practice. At the same time, the mold cavity is filled up to its edges, and the imprint is layed onto the filled cavity to form a complete model. After the hardening, the complete model is generally removed from the mold and can be cut into sections for producing a dental prosthesis or portions thereof.

One of the requirements for utilizing such dental die trays, is the ability to reposition the cut model sections back into the mold cavity. Because the model can be cut into numerous pieces, each having a unique orientation, it may be difficult to find the proper location in the mold cavity from where the particular model section was formed, which can cause a problem in producing the dental prosthesis.

Another problem with existing die trays, is that when packing the mold cavity, it is not known if the entire mold cavity has been suitably filled with plaster material. Spaces may occur in the cavity where improper filling has occurred, and these spaces may produce weakening and imperfections in the model.

One improved die tray is described in U.S. Pat. No. 4,283,173. In this patented tray, the mold cavity is formed as a hollow portion which extends entirely through the tray. The mold cavity is shaped wider at the top than at the bottom, and also includes inwardly directed ribs along the mold cavity wall. The ribs are ramp shaped inwardly sloping from the bottom of the rib to the top of the rib.

Although the use of a hollow open-ended mold cavity facilitates packing of plaster into the mold cavity, there can still be difficulty in filling the entire mold cavity adequately. Also, although the tapered shape of the mold itself as well as the sloping shape of the ribs assist in relocating the cut model sections back into the mold cavity, there still can exist some ambiguity in their proper relocation. Furthermore, because of its resilience upon the slope of the rib, the height of the tray and the mold cavity therein must be sufficient to permit the development of the rib slope and the widening of the mold cavity which results in a thick dental tray from top to bottom.

Accordingly, while the use of a die tray is extremely important in the formation of a dental prosthesis, improvements in such die trays are needed in order to facilitate the packing of the mold cavity and to improve the relocating of the cut model sections back into the mold cavity.

SUMMARY OF THE INVENTION

Accordingly, it is an object of the present invention to provide a die tray assembly which avoids the aforementioned problems of prior art devices.

Another object of the present invention is to provide a die tray assembly including a die tray, a pair of retaining arms for pivotally abutting the sides of the die tray, and a base plate for holding the die tray and the retaining arms.

Yet a further object of the present invention is to provide a dental die tray assembly which includes a die tray having a hollow arcuate mold cavity extending entirely therethrough in an upwardly widening direction from its lower to its upper surfaces.

Still a further object of the present invention is to provide a die tray assembly which includes portions thereof for identifying sections of the mold cavity to facilitate replacement of cut parts of the model back into the mold cavity.

A further object of the present invention is to provide a die tray assembly having a shorter vertical height than prior art die trays while still providing sufficient identification means for accurate refitting of the model, or cut model sections, back into the mold cavity.

Another object of the present invention is to provide a die tray assembly having a hollow mold cavity with numerous relocating structures in the mold cavity in order to facilitate replacement of the model, or cut model sections, back in the mold cavity.

A pair of removable retainer arms are pivotally coupled to the outer wall and embrace at least a portion of the body member. The arms include upper and lower lips which extend across portions of the upper and lower surfaces circumscribing the mold cavity. The upper lip also overlies a portion of the mold cavity itself for retaining the model being formed in the mold cavity.

A reversible base plate member has a substantially flat base surface on one side thereof to serve as the bottom of the mold cavity during the formation of the model. On the other side of the base plate member, pusher elements protrude therefrom for use in ejecting the hardened model from the mold cavity.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 12 is a top view of the die tray assembly ready to be filled with plaster material, including the die tray member with the retaining arms locked in place and held by the base plate member;

FIG. 13 is a cross sectional view taken along line 13—13 of FIG. 12, after the mold has been filled with plaster material and the model is formed;

FIG. 14 is a view similar to that shown in FIG. 13 with the base plate member inverted and being used to eject the hardened model from the mold cavity;

FIG. 15 is a cross sectional view showing coupling of the die tray to a conventional static centric articulator; and FIG. 16 is a cross sectional view showing the interconnection of the die tray to a dynamic functional articulator.

In the various figures of the drawing, like reference characters designate like parts.

DESCRIPTION OF THE PREFERRED EMBODIMENTS

Figure 1:
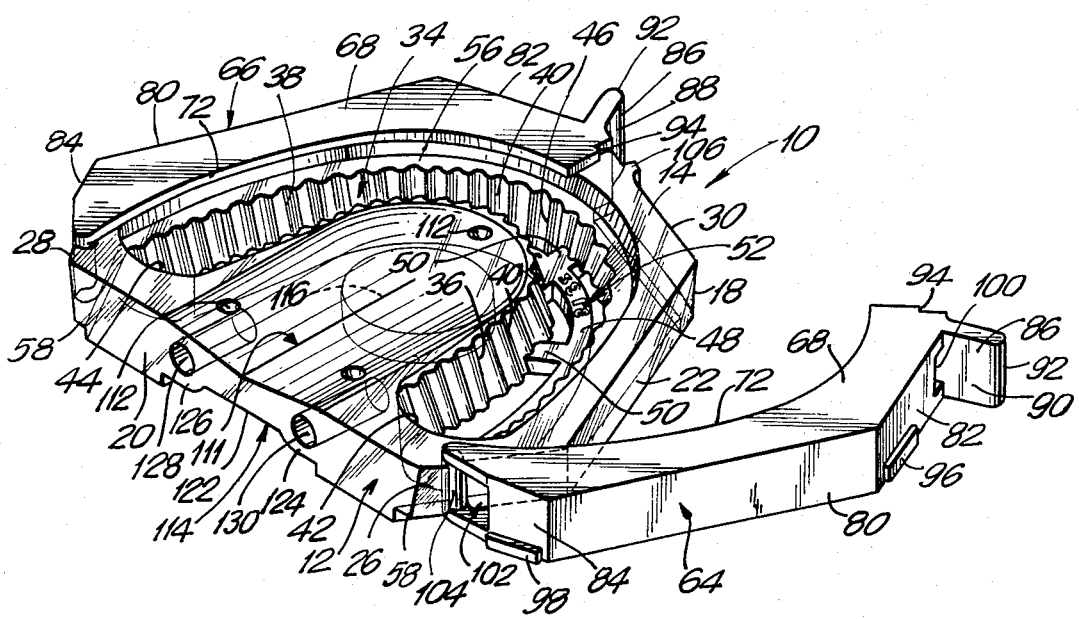
FIG. 1 is a perspective view of the dental die tray provided with the retaining arms, one of the arms being shown pivotally swung to an open position, and the other arm being shown in a closed position.
Figure 2:
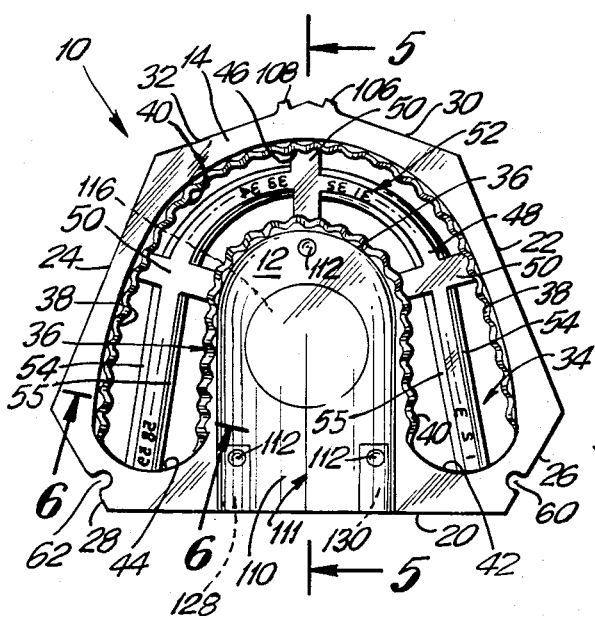
FIG. 2 is a top view of the die tray shown in FIG. 1.

Referring now to FIGS. 1-6, the die tray assembly comprises a die tray 10 formed of a body member 12 having an upper surface 14, a lower surface 16, and an outer peripheral wall 18. The peripheral wall 18 includes a front wall section 20 and side wall sections 22 and 24 which are respectively interconnected to the front wall section 20 by angled corner sections 26, 28. A rear wall is formed as a V-shape including side sections 30 and 32.

A hollow mold cavity 34 is formed entirely through the body member 12 and widens as it progresses from lower surface 16 to upper surface 14 to form an outwardly flared mold cavity whose upper end is wider than its lower end. The mold cavity 34 is arcuate in shape, substantially U-shaped, and includes an inner wall 36 and an outer wall 38. Formed along both walls 26, 38 are corrugations or teeth 40 which protrude into the mold cavity 34. The teeth 40 are of uniform projection, but sets of the teeth are wider than others. Specifically, the radius of the teeth at the distal ends 42, 44 of the mold cavity 34 is larger than the radius of the teeth formed at the medial section 46 of the mold cavity 34, so that the cut model sections can be identified by size of the ribs formed therein by the mold teeth 40, and thereby be properly refitted into the mold cavity.

Formed at the hollow bottom of the mold cavity 34 is an arcuate rib 48, substantially U-shaped, supported as an island in the hollow bottom of the mold cavity by a plurality of reinforcing webs 50. Three webs 50 are shown which interconnect the inner and outer opposing cavity walls 36, 38 and support the bottom rib 48 therebetween.

Raised indicia 52 are formed along the upper surface of the bottom rib 48 sequentially from one distal end 42 to the other distal end 44 to identify sequential sections of the mold to facilitate the refitting of the dental model back into the mold cavity 34. On one side of the rear center web 50 are placed the raised indicia from numbers 1 to 32, and on the other side of the rear center web 50 are placed the numbers 33 to 59. The rib 48 has its opposing sides 54, 55, downwardly sloped. However, the two slopes 54, 55 are at different angles, and specifically the outer most slope 54 is steeper than the inner most slope 55, thereby insuring that the refitting of the cut model sections can only be put back in one direction or position for a proper fit with respect to the different slopes.

The outer wall 38 of the mold cavity 34 is foreshortened below the inner wall 36 by means of a recessed seat 56 peripherally formed about the outer wall of the mold cavity 34 and spaced below the upper surface 14 of the die tray 10, so that the outer and inner walls of the dental model formed therein have a different configuration which can be easily identified when being refitted back into the mold cavity.

Figure 3:
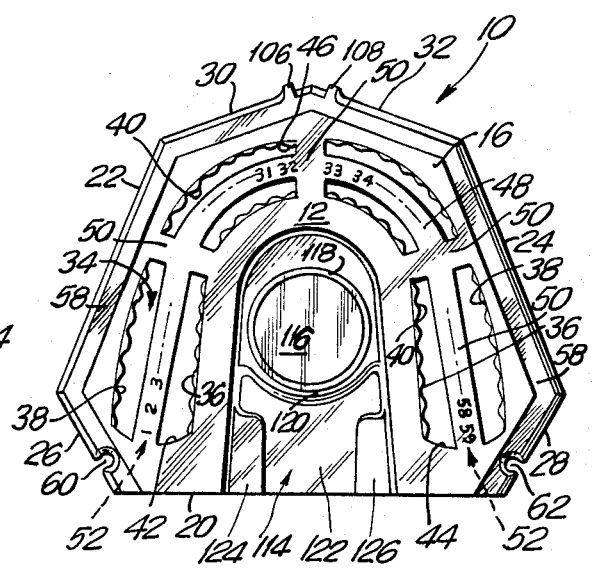
FIG. 3 is a bottom view of the die tray shown in FIG. 1.
Figure 4:
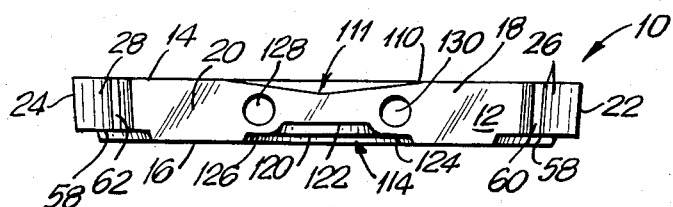
FIG. 4 is a front view of the die tray shown in FIG. 1.
Figure 6:
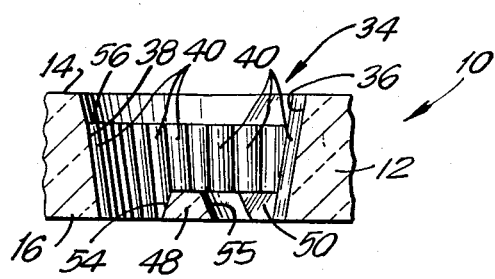
FIG. 6 is a cross sectional view taken along line 6—6 of FIG. 2, showing the inside of the mold cavity.
Figure 5:
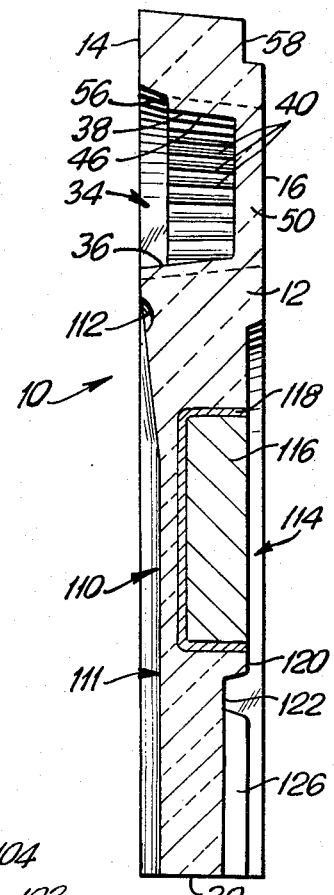
FIG. 5 is a cross sectional view taken along line 5—5 of FIG. 2.

The outer peripheral walls of the body member 12, with the exception of the front wall 20, are all inwardly tapered in a downward direction, as best seen in FIGS. 3 and 4. Additionally, an undercut 58 is formed peripherally into the lower surface 16 of the body member 12, with the exception of the front wall 20.

U-shaped sockets 60, 62 are formed in the corner wall sections 26, 28 for receiving pivot pins of the retainer arms 64, 66, as will hereinafter be explained.

Figure 7:
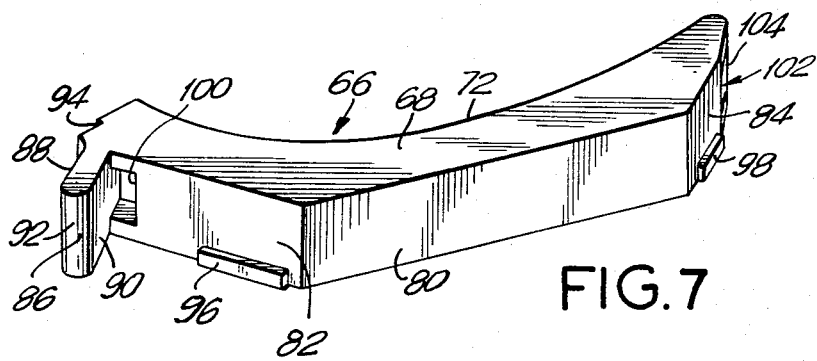
FIG. 7 is a perspective outside view of one of the retainer arms.
Figure 8:
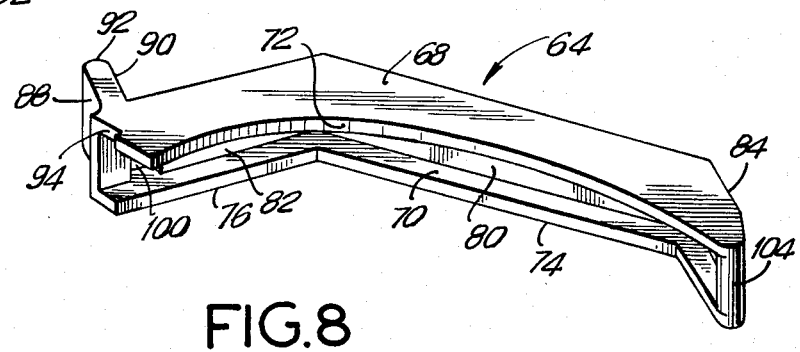
FIG. 8 is a perspective inside view of the other one of the retainer arms.

The retainer arms 64, 66 have mirror construction relative to each other, as can best be seen in FIGS. 1, 7 and 8, wherein they are shown to include arcuate shaped sections having an upper lip 68 and a lower lip 70. The upper lip 68 has an arcuate shaped distal edge 72, while the lower lip 70 includes straight line edges at the ends of a rear section 74 and two side sections 76, 78. The interconnecting sidewall between the upper and lower lips 68, 70 includes a main side section 80, a forward side section 82 and a rear side section 84.

At the front end of the arms 64, 66, a handle or tab 86 extends outwardly from the distal ends of the forward side section 82. The handle 86 includes opposing walls 88, 90 interconnected by a rounded edge 92. The base of the handle interconnects into the front part of lips 68 and 70. A step 94 is formed in the front edge of the lip 68. A rectangular protruding key 96 extends from the lower end of the forward side section 82, and a similar protruding key 98 extends from the lower end of the rear side section 84. A slot 100 is formed rearward of the handle 86 and extends through the forward side section 82.

Rear side section 84 terminates short of the ends of the upper and lower lips 68 and 70 leaving a space 102 between the upper and lower lips as best shown in FIG. 1. Interconnecting the rear ends of the lips 68, 70 is a rounded wall defining a pivot pin 104 which is received in the respective sockets 60, 62 of the die tray 10 in a snapped-in manner.

From the showings in FIGS. 1, 7 and 8, it should be appreciated that the structure of the retaining arm 64 is substantially identical to the structure of the retaining arm 66, being the mirror image thereof.

Rearwardly extending from the rear wall sections 30, 32 of the die tray 10, are protruding tangs 106 and 108 which are received, in a snapped-in manner, within the slots 100 on each of the retaining arms 64, 66. Each of the pivot pins 104 on the retaining arms 64, 66, can be removably received within the respective sockets 60, 62, being snapped in or snapped out of the sockets, to permit the retaining arms to pivot with respect to the die tray body member 12. The retainer arms 64, 66 can be secured in their closed position by swinging the retainer arms against the die tray body member 12 and locking the retainer arms when the tangs 106, 108 are snapped into the slots 100. The steps 94 permit the front part of the lips 68, 70 of the retainer arm 64 to properly abut against the front part of the lips 68, 70 of the other retainer arm 70. To open the arms, the handles 86 can be used to release the tangs 104, 106 from the slots 100 whereby the retainer arms 64, 66 can be swung outwardly away from the die tray body member 12, as shown by the retainer arm 64 in FIG. 1.

When the retainer arms 64, 66 are in their closed position, where the upper lip 68 is larger than the lower lip 70, the lip 68 not only extends onto the upper surface 14 of the die tray body member 12, but continues so that it overlies the mold cavity 34 itself. In this way, a model formed in the mold cavity 34 can be held in place by means of the retainer arms 64, 66, which serve as a lock to hold the model in place even after the model may have been cut up into sections and subsequently replaced into the mold cavity. The lower lips 70 of the retainer arms 66, 66 fit within the recesses 58 formed into the lower surface 16 of the die tray body member 12, as best shown in FIG. 13 which will be described below.

The arcuate region of the upper surface 14 of the die tray member 12, which is bounded by the mold cavity 34, defines a palate section 110. The forward portion of the palate section 110 is formed into a V-shape 111. A number of dimples 112 are also formed into the palate section, with three such dimples 112 being shown.

On the lower surface 16, the portion bounded by the mold cavity is used as an articulator connector section 114. A magnet 116 is recessed into this connector section 114 and is retained in place by means of a retainer or holder 118. The portion 120 of section 114 containing the magnet 116 is recessed, with a further recess 122 being provided and bounded by raised side shoulders 124, 126. The shoulders 124, 126 are at the same level as recessed portion 120. Formed into the front surface 20 of the body member 12 are two apertures 128, 130 for use in interconnecting to an articulator, as will hereinafter be explained.

Figure 9:
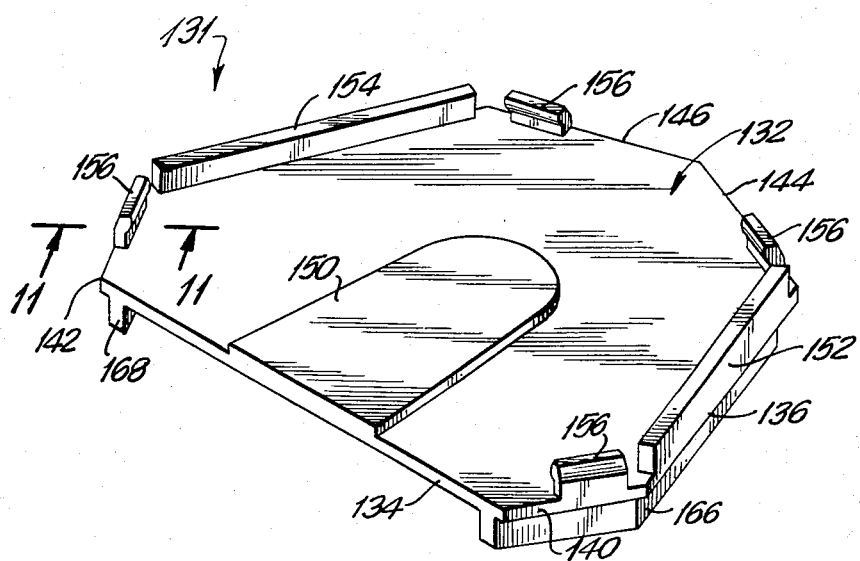
FIG. 9 is a perspective view showing the top of the base plate member.
Figure 10:
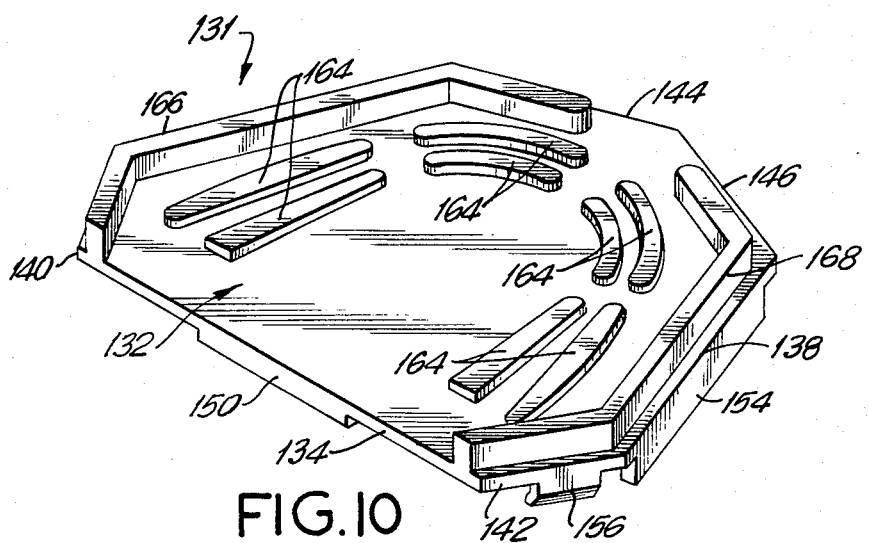
FIG. 10 is a perspective view showing the reverse bottom side of the base plate member.

Referring now to FIGS. 9 and 10, there is shown a base plate member 131 which is utilized in conjunction with the die tray body member and retainer arms, heretofore described. The base plate member 131 includes a substantially flat plate 132 whose outer peripheral edge conforms to the periphery of the die tray body member 12, but is slightly larger on all sides to allow for the retainer arms 64, 66, as set forth below. The peripheral edge includes a straight front edge 134, side edges 136 and 138 interconnected by the corner angled edges 140, 142, and V-shaped rear edges 144, 146.

Figure 11:
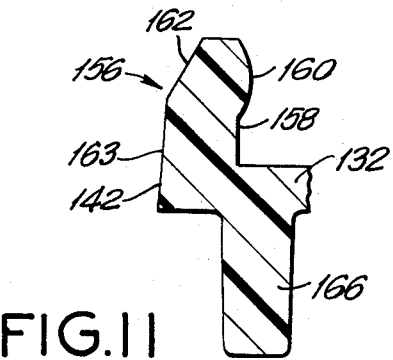
FIG. 11 is a cross sectional view taken along line 11—11 of FIG. 9.

One side of the plate 132, as shown in FIG. 9 serves as the base for the mold cavity 34. This side has a surface which is substantially flat, with the exception of the raised arcuate boss 150 which conforms in shape to the arcuate mounting surface 114 on the lower surface 16 of the die tray body member 12, as heretofore described. Upstanding side ledges 152, 154 extend perpendicularly from the side edges 136, 138 of the base plate member 131. Upwardly extending from the corner angled edge 140, 142, as well as from the rear V-shaped rear edges 144, 146 are four substantially identical locking wall sections 156. As can best be seen in FIG. 11, the locking wall sections 156 include an undercut portion 158 on the lower part of the inner side of the wall and a protruding cam surface 160 on the upper part of the inner side of the wall. The outer edge 162 of the wall is angled downwardly into an outwardly tapering outer surface 163.

The locking wall sections 156 form keyways for receiving the protruding keys 96, 98 on the retaining arms 64, 66, as will hereinafter be described.

On the reverse side of the base plate member 131, there are formed protruding pusher sections 164. The pusher sections 164 are shaped to fit into the open bottom of the mold cavity 34 on either side of the bottom rib 48. A three sectioned peripheral wall 166 is formed on one edge of the pusher side, and a similar upstanding three sectional peripheral wall 168 is formed at the other edge of the pusher side. Both peripheral walls 166, 168 are inwardly spaced from the edge of the base plate member 131.

Referring now to FIGS. 12–14, there is shown the assembly of the die tray with the pivotally connected retainer arms 64, 66 placed onto the body plate member 131. The retainer arms 64, 66 closed against the die tray body member 12 so that the tangs 104, 106 are received within the appropriate slots 100 on the arms 64, 66 and the arms 64, 66 are thereby held in place. The die tray body member 12 with the retainer arms 64, 66 are then snap fit into the base plate member 131. The arcuate boss 150 on the base plate member 131 is received within the appropriate recess 114 provided on the underside of the die tray body member 12. The side walls 152, 154 of the base plate member 131 hold the retainer arms 64, 66. Each of the locking wall sections 156 receive a corresponding projecting key 96, 98 on the retainer arms 64, 66, which are snap-fit in the undercut 158 on each of the wall sections 156 to prevent lifting off of the die tray body member 12. The handles 86 of the retainer arms extend outwardly over the V-shaped rear edges 144, 146 of the base plate member 131.

Once assembled, the retainer arms 64, 66 are securely held in place and the base plate member 131 will also be held securely positioned at the bottom of the mold cavity 34. However, it should be appreciated that the base plate member does not form an air-tight seal at the bottom of the mold cavity.

After assembly, the appropriate model 165 can be formed, as shown in FIG. 13, where the walls 166, 168 are placed on a flat surface. It should be noted, that in the formation of the model, the plaster material is pushed into the mold cavity 34. Some plaster material can squeeze between the base plate member 131 and the die tray body member 12 to be sure that enough plaster material is provided to fill the entire mold cavity. Additionally, it should be noted in FIG. 13, that the top lips 68 of the retainer arms 64, 66 overlie the mold cavity 34 so as to form a shoulder formation in the model. This will help to retain the completed model when replaced in the mold cavity.

After the model 165 has been formed, the base plate member 131 is removed and the retainer arms 64, 66 are also removed. The base plate member 131 is then inserted so that the pusher members 164 extend upwardly and the side walls 152, 154 rest on a flat surface. The base plate member 131 is positioned under the die tray 10 so that the pushers 164 will fit on either side of the rib 48 at the bottom of the mold cavity 34 and serve to eject the model 165 upwardly from the mold cavity, as shown in FIG. 14, as the die tray 10 is being pushed downwardly onto the base plate member 131, which downward pushing is made easier by the tapered outer walls of the die tray 10, as set forth above.

The die tray assembly of the present invention is so arranged as to facilitate the formation of the model and to permit easy reinsertion of the model back into the mold cavity. Normally, after the model has been made, it is cut into sections in order to produce the prosthetic device from the model. However, it is often necessary to refit the model, either in whole or in its individual sections, back into the mold cavity.

The present invention facilitates such replacement. Firstly, it should be appreciated that the outer wall of the mold cavity is shorter because of the recessed seat 56 formed thereabout. This seat forms an indentation in the outer periphery of the model. Accordingly, when each model section is reinserted back into the mold cavity, assurance will be had that the proper back and front orientation is achieved since the corresponding indentation must sit in the seat formed at the outer wall of the mold cavity.

Additionally, the radius of the teeth vary between the distal and medial portions of the arcuate mold cavity. As a result, any particular model section does not fit into any other section because the radius of the grooves formed into the model by means of the teeth, will not match the teeth in the other section of the mold cavity. Also because of the raised indicia provided on the bottom rib, numbers will be directly molded into the model and the proper numeric section can be read on the model and matched with the numbers on the rib.

Furthermore, because the bottom rib has different sloped surfaces on either side, when the model section is reinserted, if not positioned properly in its place, the angles of the model will not match the angle on the side sloped wall of the bottom rib.

The presence of the retainer arms overhanging the mold cavity serves to provide a suitable shoulder on the upper surface of the model which will again reinsure proper placement when the retainer arms are used to hold the model sections in place.

Because of the various construction features heretofore described, the reinsertion of the model, or model sections, with their proper orientation is assured. Accordingly, the actual height of the die tray body can be made shorter than in prior art. In prior art systems, the die tray had to be of considerable height in order to provide for adequate assurance of proper reinsertion. Because of the various other means provided, as heretofore described, with the present die tray assembly, the model sections can be refitted without difficulty, even though the die tray walls are short.

When forming a model of the lower teeth portion, the model would appear similar to that shown in FIGS. 13 and 14. However, when forming a model of the upper teeth portion, it is often desirable to also include a model of the palate. For this reason, the arcuate section 110 on the upper surface 14 of the die tray body member 12, is so shaped as to reassure proper placement of the palate model section. The V-notch 111 as well as the plurality of appropriately spaced apart dimples 112 are used for this purpose. After the palate has been formed as part of the model, when it is desirable to reinsert it, the V-shaped notch 111 and the dimples 112 will reassure such appropriate reinsertion. A palate model section 169 is indicated in FIG. 15, as set forth below.

As is well known in the art, after the proper upper and lower models are formed, the die tray assembly is often mounted onto an articulator for suitable positioning of the upper and lower models with respect to each other. The apertures 128, 130 formed into the front wall 20 of the die tray body member 12, having the palate model section 169 thereon, can be utilized for receiving a pin 170 of a conventional static centric articulator 172 as shown in FIG. 15. Such articulators just have pivoted motion up and down and accordingly it is sufficient to provide the apertures 128, 130 for such purpose.

The use of the magnet 116 is available for interconnecting the die tray 10 onto the metal plate or keeper 174 of a dynamic functional articulator which provides numerous types of movements of the model sections formed. As shown in FIG. 16, the keeper 174 is secured in plaster material 176, such plaster material 176 being conventional in dynamic functional articulators for determining the proper position of the die tray. Once the plaster material 176 is formed, the recesses 120 and 122 of the die tray 10 properly position the die tray 10 thereon, whereby the die tray 10 can be removed and properly remounted on the articulator as many times as necessary.

It is noted, that FIG. 16 shows the die tray 10 mounted upside down on the articulator, where the upper model is disposed therein. Accordingly, the retainer arms 64, 66 are used to hold the upper model, and more particularly the cut model sections, within the die tray 10 in this upside down position, in the manner set forth above.

The fact that the hollow mold cavity 34 is open at the top and the bottom thereof, is an important feature of the present invention, whereby this feature enables the mold cavity 34 to be completely cleaned after use thereof. It is noted, that in the prior art trays having a mold cavity with a closed bottom, it is difficult to clean the prior art mold cavity. Accordingly, debris is often left in the prior art mold cavity after use thereof, because of the difficulty in cleaning the closed bottom. This debris accumulates and builds up within the closed bottom of the prior art mold cavity, thereby creating a misfit between the model and the prior art mold cavity, whereby the models formed thereby are not accurate and have built-in errors therein. These built-in errors are avoided by the completely opened mold cavity of the present invention.

It is noted, that if desired, only one side of the die tray 10, or a portion thereof, may be used to form a partial model, whereby the retainer arm 64 or 66 on the selected side would be used to hold the partial model, or cut sections thereof, in position within the selected side. However, if desired, the die tray 10 of the present invention could be formed as two separate sections or pieces, a left die tray section having the retainer arm 66 thereon and an unattached right die tray section having the retainer arm 64 thereon, for use in forming partial models, where the structure thereof is easily understood so that a showing thereof is not thought necessary.

Typically, the die tray assembly heretofore described would be formed of plastic material. The die tray 10 is preferably transparent, so that it is possible to view the contents of the mold cavity as it is being filled and be sure that the plaster suitably fills the mold cavity, as desired.

Numerous alterations of the structure herein disclosed will suggest themselves to those skilled in the art. However, it is to be understood that the present disclosure relates to preferred embodiments of the invention which are for purposes of illustration only and are not to be construed as a limitation of the invention.

What is claimed is:

1. A die tray assembly for production of a dental working model, comprising:
a tray body member having upper and lower surfaces, and a peripheral outer wall;

a hollow arcuate mold cavity extending entirely through said tray body member in an upwardly widening direction from said lower surface to said upper surface, said mold cavity being bounded by facing outer and inner cavity walls;

continuous teeth disposed on said facing cavity walls and extending into said mold cavity; and an arcuate rib supported as an island at a bottom of said mold cavity, said rib including identifying means for easily reinserting the model back into said mold cavity.

2. A die tray assembly as in claim 1, and comprising webs extending between said facing cavity walls and supporting said rib.

3. A die tray assembly as in claim 1, wherein said identifying means include raised indicia sequentially positioned along an upper surface of said rib for being cast into the model formed in said cavity, to thereby identify sections of the model for repositioning the model sections back into the mold cavity.

4. A die tray assembly as in claim 1, wherein said identifying means include two sides of said rib being downwardly sloped at respective different slope angles to provide a keyed pattern for returning model sections back into the cavity with proper orientation.

5. A die tray assembly as in claim 1, wherein a radius of said teeth at distal portions of said arcuate mold cavity is greater than a radius of said teeth at a medial portion of said arcuate mold cavity so that cut model sections can be identified for proper reinsertion back into said mold cavity.

6. A die tray assembly as in claim 1, and comprising a palate section provided in said upper surface of said tray body member and bounded by said mold cavity, at least a portion of said palate section having a V-shape, and a plurality of dimples provided in said palate section, said V-shape and said dimples facilitating reinsertion of a palate portion of the model formed in said body member.

7. A die tray assembly as in claim 1, and comprising a mounting magnet disposed in said lower surface of said tray body member for mounting onto an articulator.

8. A die tray assembly as in claim 1, wherein a portion of said lower surface is bounded by said mold cavity, said lower surface portion being recessed.

9. A die tray assembly as in claim 1, and comprising a pair of positioning apertures extending into a forward end of said peripheral outer wall for mounting said tray body member onto an articulator.

10. A die tray assembly as in claim 1, and comprising a pair of removable retainer arms pivotally coupled to respective side portions of said peripheral outer wall, said retainer arms embracing at least a portion of said tray body member circumscribing said mold cavity.

11. A die tray assembly as in claim 1, including seat means for identifying an outer wall of the model so that the model can be reinserted easily back into said mold cavity, said outer cavity wall being foreshortened by a recessed seat bounding an outer periphery of said mold cavity to provide said seat means.

12. A die tray assembly as in claim 1, wherein said die tray assembly is fabricated from a plastic material.

13. A die tray assembly for production of a dental working model, comprising:

a tray body member having upper and lower surfaces, and a peripheral outer wall;

a hollow arcuate mold cavity extending entirely through said tray body member in an upwardly widening direction from said lower surface to said upper surface, said mold cavity being bounded by facing outer and inner cavity walls;

continuous teeth disposed on said facing cavity walls and extending into said mold cavity; and retaining means for holding the model when reinserted back into said mold cavity, said retaining means including a pair of removable retainer arms pivotally coupled to respective side portions of said peripheral outer wall, said retainer arms embracing at least a portion of said tray body member circumscribing said mold cavity;

said peripheral outer wall including a front section, opposing side sections and a rear section, said upper and lower surfaces including respective upper and lower ledges circumscribing said mold cavity, said retainer arms including upper and lower lips for respectively engaging said upper and lower ledges;

first means for removably securing said retainer arms to said tray body member to permit pivotal movement of said retainer arms relative to said tray body member, said first means including a pivot pin provided adjacent one end of each retainer arm, and a socket respectively provided in each side section of said peripheral outer wall adjacent said front section for receiving said pivot pin of the respective retainer arm; and second means for locking said retainer arms in a retaining position against said peripheral outer wall of said tray body member, said second means including a pair of spaced apart tangs outwardly extending from said rear section of said peripheral outer wall, and each of said retainer arms including a slot adjacent an opposite end of each retainer arm for engaging a respective one of said tangs to lock said retainer arms in said retaining position, and handle means on each retainer arm for pivotally releasing said retainer arms for said retaining position.

14. A die tray assembly as in claim 13, wherein said upper lips extends across said upper ledge and overlies a portion of said mold cavity for retaining the model when formed in said mold cavity.

15. A die tray assembly as in claim 13, and comprising a peripheral undercut provided in said lower ledge for receiving said lower lip.

16. A die tray assembly for production of a dental working model, comprising:

a tray body member having upper and lower surfaces, and a peripheral outer wall;

a hollow arcuate mold cavity extending entirely through said tray body member in an upwardly widening direction from said lower surface to said upper surface, said mold cavity being bounded by facing outer and inner cavity walls;

continuous teeth disposed on said facing cavity walls and extending into said mold cavity; and a reversible base plate member having a substantially flat base surface on one side to serve as a bottom for said mold cavity during formation of the model, and pusher members protruding from an opposite side of said base plate member for ejecting the model from said mold cavity.

17. A die tray assembly as in claim 16, and comprising a pair of retainer arms pivotally coupled to said tray body member and snugly embracing said peripheral outer wall, and wherein said base plate member includes an upstanding peripheral wall disposed about said flat base surface for holding said retainer arms in position against said tray body member.

18. A die tray assembly as in claim 17, and comprising keys projecting outwardly from said retainer arms, and undercut keyways provided in sections of said upstanding peripheral wall for receiving said keys to provide a snap fit between said base plate member and said retainer arms.

19. A die tray assembly as in claim 17, wherein said upstanding peripheral wall includes spaced apart sections to provide resiliency for securing said base plate member to said tray body member and retainer arms.

20. A die tray assembly as in claim 16, wherein said tray body member includes an arcuate recess in said lower surface bounded by said mold cavity, and wherein said base surface of said base plate member includes an arcuate boss for insertion in said arcuate recess to position said base plate member during formation of the model.

21. A die tray assembly as in claim 16, wherein said pusher members include projecting arcuate pusher segments for insertion into said mold cavity.

22. A die tray assembly as in claim 21, and comprising an arcuate rib supported as an island at a bottom of said mold cavity, and wherein said pusher segments fit into the bottom of said mold cavity on either side of said arcuate rib.

23. A die tray assembly as in claim 16, and comprising an upstanding peripheral wall provided about said opposite side of said base plate member for retaining said tray body member during ejection of the model therefrom.

24. A die tray assembly for the production of a dental working model, comprising:
   a tray body member having upper and lower surfaces, and a peripheral outer wall;
   an arcuate mold cavity extending entirely through said tray body member; and
   a reversible base plate member having a substantially flat base surface on one side to serve as a bottom for said mold cavity during formation of the model, and pusher members protruding from an opposite side of said base plate member for ejecting the model from said mold cavity.

25. A die tray assembly as in claim 24, including a pair of retainer arms pivotally coupled to said peripheral outer wall and embracing at least a portion of said tray body member around said mold cavity.

26. A die tray assembly as in claim 25, and comprising an upstanding peripheral wall disposed about said flat base surface for holding said retainer arms in position against said tray body member.

27. A die tray assembly as in claim 24, wherein said die tray assembly is fabricated from a plastic material.

28. A die tray assembly for the production of a dental working model, comprising:
   a tray body member having upper and lower surfaces, and a peripheral outer wall;
   an arcuate mold cavity provided in said tray body member; and
   retaining means for holding the model when reinserted back into said mold cavity, said retaining means including a pair of removable retainer arms pivotally coupled to respective side portions of said peripheral outer wall, said retainer arms embracing at least a portion of said tray body member circumscribing said mold cavity;
   said peripheral outer wall including a front section, opposing side sections and a rear section;
   first means for removably securing said retainer arms to said tray body member to permit pivotal movement of said retainer arms relative to said tray body member, said first means including a pivot pin provided adjacent one end of each retainer arm, and a socket respectively provided in each side section of said peripheral outer wall adjacent said front section for receiving said pivot pin of the respective retainer arm; and
   second means for locking said retainer arms in a retaining position against said peripheral outer wall of said tray body member, said second means including a pair of spaced apart tangs outwardly extending from said rear section of said peripheral outer wall, and each of said retainer arms including a slot adjacent an opposite end of each retainer arm for engaging a respective one of said tangs to lock said retainer arms in said retaining position, and handle means on each retainer arm for pivotally releasing said retainer arms from said retaining position.

29. A die tray assembly as in claim 28, wherein said upper and lower surfaces include define respective upper and lower ledges, and wherein said retainer arms include upper and lower lips for respectively engaging said upper and lower ledges, said upper lips extending across said upper ledge and overlying a portion of said mold cavity for removably retaining the model formed in said mold cavity.

30. A die tray assembly for the production of a dental working model, comprising:
   a tray body member having upper and lower surfaces, and a peripheral outer wall;
   an arcuate mold cavity provided in said tray body member; and
   retaining means for holding the model when reinserted back into said mold cavity, said retaining means including a pair of removable retainer arms coupled to respective opposing side portions of said peripheral outer wall, said retainer arms embracing at least a portion of said tray body member circumscribing said mold cavity;
   said upper and lower surfaces including respective upper and lower edges circumscribing said mold cavity, said retainer arms including upper and lower lips for respectively engaging said upper and lower edges; and
   means for individually removably securing each of said retainer arms independent of each other in a retaining position against said respective opposing side portions of said peripheral outer wall of said tray body member so that one of said retainer arms can be secured on said tray body member when the other retainer arm has been removed from said tray body member.

31. A die tray assembly as in claim 30, including means to permit pivotal movement of at least a portion of each of said retainer arms relative to said tray body member in directions towards and away from each other.

32. A die tray assembly as in claim 30, including means on each retainer arm for gripping to pivotally release each said retainer arm from said retaining position.

33. A die tray assembly as in claim 30, wherein said mold cavity is bounded by facing outer and inner cavity walls, and continuous teeth are disposed on said facing cavity walls, said teeth extending into said mold cavity.

* * * * *